United States Patent
Terentiev (12)

(10) Patent No.: US 6,416,215 B1
(45) Date of Patent: Jul. 9, 2002

(54) PUMPING OR MIXING SYSTEM USING A LEVITATING MAGNETIC ELEMENT

(75) Inventor: Alexandre N. Terentiev, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/460,600

(22) Filed: Dec. 14, 1999

(51) Int. Cl.$^7$ .......................... B01F 13/08; H01L 39/00; B04F 17/00
(52) U.S. Cl. ...................... 366/273; 505/166; 417/420; 366/274
(58) Field of Search ................................ 366/273, 274, 366/331, 325.5; 416/3, 500; 310/93, 103, 90.5; 417/420; 505/879, 888, 889, 892, 910, 911, 166, 165

(56) References Cited

U.S. PATENT DOCUMENTS

| | | | |
|---|---|---|---|
| 2,506,886 A | | 5/1950 | Okulitch |
| 2,733,857 A | * | 2/1956 | Beams ...................... 310/90.5 |
| 2,810,556 A | * | 10/1957 | Zozulin |
| 3,110,481 A | * | 11/1963 | Kivenson .................... 366/273 |
| 3,187,235 A | * | 6/1965 | Berlincourt et al. ........ 505/879 |

(List continued on next page.)

FOREIGN PATENT DOCUMENTS

| | | |
|---|---|---|
| DE | 3927045 | 7/1990 |
| DE | 4201693 | 4/1993 |
| DE | 4413463 | 10/1995 |
| DE | 19643844 | 5/1998 |
| FR | 2696949 | 4/1994 |

OTHER PUBLICATIONS

O'Connor, Leo, "Active Magnetic Bearings Give Systems a Lift," Mechanical Engineering, American Society of Mechanical Engineers (New York), vol. 114 (No. 7), p. 52, (Jul. 1, 1992).

(List continued on next page.)

*Primary Examiner*—Tony G. Soohoo (57) ABSTRACT

A system capable of pumping or mixing relatively warm fluids using a rotating magnetic element or bearing levitated by a cold superconducting element is disclosed. The magnetic element or bearing carries at least one impeller and is placed in a fluid vessel positioned external to the outer wall of a cryostat or other housing for the superconducting element. A separate cooling source thermally linked to the superconducting element provides the necessary cooling to create the desired superconductive effects and induce levitation in the magnetic element or bearing. The outer wall or housing defines a chamber around the cold superconducting element that thermally isolates it from the vessel. To ensure that the desired level of thermal isolation is provided, this chamber is evacuated or filled with an insulating material. This thermal isolation allows for placement of the superconducting element in close proximity to the wall or housing adjacent to the vessel to achieve a significant reduction in the separation distance from the magnetic element or bearing. This enhances the magnetic stiffness and loading capacity of the levitating element or bearing. However, since the superconducting element is thermally isolated from the outer wall or housing, the vessel, and hence the magnetic element/bearing and fluid contained therein, are not exposed to the cold temperatures required to produce the desired superconductive effects and the resultant levitation. By using means external to the vessel to rotate and/or stabilize the magnetic element/bearing levitating in the fluid, the desired pumping or mixing action is provided.

60 Claims, 5 Drawing Sheets

U.S. PATENT DOCUMENTS

| | | | |
|---|---|---|---|
| 3,187,236 A | * 6/1965 | Leslie | 505/879 |
| 3,422,765 A | 1/1969 | Schoch | |
| 3,438,328 A | * 4/1969 | Laing | |
| 3,598,456 A | * 8/1971 | Love | 310/90.5 |
| 3,608,088 A | 9/1971 | Dorman et al. | |
| 3,647,324 A | 3/1972 | Rafferty et al. | |
| 3,650,581 A | 3/1972 | Boden et al. | |
| 3,689,033 A | * 9/1972 | Holmstrom et al. | 366/273 |
| 3,771,910 A | 11/1973 | Laing | |
| 3,778,122 A | * 12/1973 | Doll et al. | |
| 3,888,466 A | 6/1975 | Sedam | |
| 3,981,803 A | 9/1976 | Coulthard | |
| 4,044,567 A | 8/1977 | Dix et al. | |
| 4,080,112 A | 3/1978 | Zimmerman | |
| 4,090,745 A | 5/1978 | Dohogne et al. | |
| 4,116,017 A | * 9/1978 | Oberpriller | 505/888 |
| 4,123,676 A | 10/1978 | Cooper et al. | |
| 4,135,253 A | 1/1979 | Reich et al. | |
| 4,184,090 A | 1/1980 | Taiani et al. | |
| 4,185,617 A | 1/1980 | Hutchins | |
| 4,199,265 A | 4/1980 | Sanderson et al. | |
| 4,204,774 A | 5/1980 | de Bruyne | |
| 4,209,259 A | 6/1980 | Rains et al. | |
| 4,247,792 A | 1/1981 | Klicks et al. | |
| 4,264,215 A | 4/1981 | Nunlist et al. | |
| 4,266,950 A | 5/1981 | Makino et al. | |
| 4,274,022 A | 6/1981 | Elsel | |
| 4,300,356 A | * 11/1981 | Notaro et al. | 505/888 |
| 4,339,680 A | 7/1982 | Flecher et al. | |
| 4,355,906 A | 10/1982 | Ono | |
| 4,363,773 A | * 12/1982 | Mine | 505/879 |
| 4,365,942 A | 12/1982 | Schmidt | |
| 4,390,283 A | * 6/1983 | Meyer | |
| 4,417,772 A | 11/1983 | Robinson | |
| 4,483,623 A | 11/1984 | Eaton et al. | |
| 4,498,785 A | 2/1985 | de Bruyne | |
| 4,526,015 A | 7/1985 | Laskaris | |
| 4,557,377 A | 12/1985 | Maloney | |
| 4,568,195 A | 2/1986 | Herz et al. | |
| 4,591,357 A | 5/1986 | Sneider | |
| 4,674,960 A | 6/1987 | Rando et al. | |
| 4,678,409 A | 7/1987 | Kurokawa | |
| 4,688,998 A | 8/1987 | Olsen et al. | |
| 4,711,582 A | 12/1987 | Kennedy | |
| 4,725,207 A | 2/1988 | Buchwald et al. | |
| 4,727,724 A | 3/1988 | Intichar et al. | |
| 4,759,635 A | 7/1988 | MacMichael et al. | |
| 4,770,007 A | 9/1988 | Murai et al. | |
| 4,779,614 A | 10/1988 | Moise | |
| 4,797,386 A | 1/1989 | Gyorgy et al. | |
| 4,850,821 A | 7/1989 | Sakai | |
| 4,878,351 A | 11/1989 | Weber et al. | |
| 4,892,863 A | 1/1990 | Agarwala | |
| 4,913,555 A | 4/1990 | Maeda et al. | |
| 4,960,521 A | 10/1990 | Keller | |
| 4,984,972 A | 1/1991 | Clausen et al. | |
| 4,993,840 A | 2/1991 | Maeda et al. | |
| 4,993,841 A | 2/1991 | Lofgren et al. | |
| 5,001,448 A | 3/1991 | Srivastava et al. | |
| 5,032,869 A | 7/1991 | Herd et al. | |
| 5,040,898 A | 8/1991 | Sweatman et al. | |
| 5,045,074 A | 9/1991 | Satterfield et al. | |
| 5,055,005 A | 10/1991 | Kletschka | |
| 5,061,679 A | 10/1991 | Weeks, II | |
| 5,078,969 A | 1/1992 | Bacus | |
| 5,089,017 A | 2/1992 | Young et al. | |
| 5,094,084 A | 3/1992 | Mraz | |
| 5,096,390 A | 3/1992 | Sevrain et al. | |
| 5,106,273 A | 4/1992 | Lemarquand et al. | |
| 5,112,202 A | 5/1992 | Oshima et al. | |
| 5,113,165 A | * 5/1992 | Ackermann | 505/879 |
| 5,126,317 A | 6/1992 | Agarwala | |
| 5,126,611 A | 6/1992 | Armstrong et al. | |
| 5,140,823 A | 8/1992 | Mraz | |
| 5,141,327 A | * 8/1992 | Shiobara | |
| 5,152,679 A | 10/1992 | Kanemitsu et al. | |
| 5,159,219 A | 10/1992 | Chu et al. | |
| 5,183,336 A | 2/1993 | Poltorak et al. | |
| 5,195,877 A | 3/1993 | Kletschka | |
| 5,197,865 A | 3/1993 | Sevrain et al. | |
| 5,211,546 A | 5/1993 | Isaacson et al. | |
| 5,240,322 A | 8/1993 | Haber et al. | |
| 5,240,323 A | 8/1993 | Haber et al. | |
| 5,256,638 A | 10/1993 | Weinberger et al. | |
| 5,267,791 A | 12/1993 | Christian et al. | |
| 5,298,875 A | * 3/1994 | Laibowitz et al. | 505/879 |
| 5,313,130 A | 5/1994 | Shibayama et al. | |
| 5,316,440 A | 5/1994 | Kijima et al. | |
| 5,325,002 A | 6/1994 | Rabinowitz et al. | |
| 5,330,967 A | 7/1994 | Takahata et al. | |
| 5,350,283 A | 9/1994 | Nakazeki et al. | |
| 5,352,036 A | 10/1994 | Haber et al. | |
| 5,368,390 A | 11/1994 | Gambrill et al. | |
| 5,382,833 A | 1/1995 | Wirges | |
| 5,385,546 A | 1/1995 | Kriesel et al. | |
| 5,385,564 A | 1/1995 | Slater et al. | |
| 5,393,142 A | 2/1995 | Meier | |
| 5,399,074 A | 3/1995 | Nose et al. | |
| 5,402,648 A | 4/1995 | Longsworth | |
| 5,405,251 A | 4/1995 | Sipin | |
| 5,407,272 A | 4/1995 | Meier | |
| 5,411,378 A | 5/1995 | Sipin | |
| 5,438,038 A | 8/1995 | Takahata et al. | |
| 5,451,524 A | 9/1995 | Coble et al. | |
| 5,470,152 A | 11/1995 | Rains | |
| 5,470,208 A | 11/1995 | Kletschka | |
| 5,478,149 A | 12/1995 | Quigg | |
| 5,517,071 A | 5/1996 | Moon | |
| 5,524,441 A | 6/1996 | Herrmann et al. | |
| 5,525,849 A | 6/1996 | Ito et al. | |
| 5,527,159 A | 6/1996 | Bozeman, Jr. et al. | |
| 5,533,804 A | 7/1996 | Larsson et al. | |
| 5,540,116 A | 7/1996 | Hull et al. | |
| 5,547,280 A | 8/1996 | Wanninger et al. | |
| 5,567,672 A | 10/1996 | Terentiev et al. | |
| 5,575,630 A | 11/1996 | Nakazawa et al. | |
| 5,581,135 A | 12/1996 | Ito et al. | |
| 5,586,823 A | 12/1996 | Carr | |
| 5,599,175 A | 2/1997 | Tojo et al. | |
| 5,611,679 A | 3/1997 | Ghosh et al. | |
| 5,633,548 A | 5/1997 | Takahata et al. | |
| 5,658,136 A | 8/1997 | Mendler | |
| 5,676,462 A | 10/1997 | Fraczek et al. | |
| 5,678,306 A | 10/1997 | Bozeman, Jr. et al. | |
| 5,683,231 A | 11/1997 | Nakazawa et al. | |
| 5,692,882 A | 12/1997 | Bozeman, Jr. et al. | |
| 5,703,424 A | 12/1997 | Dorman | |
| 5,710,469 A | 1/1998 | Ries | |
| 5,719,455 A | 2/1998 | Higasa et al. | |
| 5,722,303 A | 3/1998 | Hull et al. | |
| 5,725,357 A | 3/1998 | Nakazeki et al. | |
| 5,747,426 A | 5/1998 | Abboud | |
| 5,757,098 A | 5/1998 | Higuchi et al. | |
| 5,758,965 A | 6/1998 | Gambrill et al. | |
| 5,763,971 A | 6/1998 | Takahata et al. | |
| 5,779,359 A | 7/1998 | Gambrill et al. | |
| 5,789,837 A | 8/1998 | Shin et al. | |
| 5,794,802 A | 8/1998 | Caola | |
| 5,801,469 A | 9/1998 | Takahata et al. | |
| 5,831,362 A | 11/1998 | Chu et al. | |
| 5,848,523 A | 12/1998 | Gamble et al. | |

| | | | |
|---|---|---|---|
| 5,856,719 A | | 1/1999 | De Armas |
| 5,861,574 A | * | 1/1999 | Kotani et al. ................ 505/888 |
| 5,911,558 A | | 6/1999 | Nakazeki et al. |
| 5,923,109 A | | 7/1999 | Higuchi et al. |
| 5,941,867 A | | 8/1999 | Kao |
| 5,947,703 A | | 9/1999 | Nojiri et al. |
| 5,957,672 A | | 9/1999 | Aber |
| 5,961,213 A | | 10/1999 | Tsuyuki et al. |
| 5,985,535 A | * | 11/1999 | Urabe |
| 6,015,272 A | | 1/2000 | Antaki et al. |
| 6,015,275 A | | 1/2000 | Sukuki et al. |
| 6,024,542 A | | 2/2000 | Phillips et al. |
| 6,030,188 A | | 2/2000 | Nojiri et al. |
| 6,050,782 A | | 4/2000 | Lembke |
| 6,065,865 A | | 5/2000 | Eyraud et al. |
| 6,071,093 A | | 6/2000 | Hart |
| 6,074,180 A | | 6/2000 | Khanwilkar et al. |
| 6,095,677 A | | 8/2000 | Karkos, Jr. et al. |
| 6,100,618 A | | 8/2000 | Schoeb et al. |
| 6,107,905 A | * | 8/2000 | Itoh et al. ................... 505/892 |
| 6,118,199 A | | 9/2000 | Lembke |
| 6,121,704 A | | 9/2000 | Fukuyama et al. |
| 6,129,660 A | | 10/2000 | Nakazeki et al. |
| 6,135,729 A | | 10/2000 | Aber |
| 6,147,425 A | | 11/2000 | Ucyama et al. |
| 6,206,562 B1 | | 3/2001 | Eyraud et al. |
| 6,208,051 B1 | | 3/2001 | Ando |

OTHER PUBLICATIONS

Hull, John, R., "Superconducting Bearings," Superconductor Science and Technology, vol. 13, No. 2, (pp. R1–R15).

Tixador, Pascal; Tempe, Alexis; Gautier–Picard, Pierre; Chaud, X.; Beaugnon, Eric, "Electrical Motor with Bulk Y–Ba–Cu–O Pellets," IEEE Transactions on Applied Superconductivity, vol. 7, No. 2, Jun. 1997, (pp. 896–899).

Tixador, P.; Hiebel, E.; Chaud, X.; Beaugnon, E., "Superconducting Coupling Device," Cryogenics 1995, vol. 35, No. 9, (pp. 567–572).

* cited by examiner

PUMPING OR MIXING SYSTEM USING A LEVITATING MAGNETIC ELEMENT

This application claims the benefit of U.S. Provisional Patent Application Ser. No. 60/114,655, filed Jan. 4, 1999, entitled "Pump for Ultra-Pure or Hazardous Fluids Based on Non-Contact Superconducting Bearing."

TECHNICAL FIELD

The present invention relates to the use of rotating, levitating magnetic elements for mixing or pumping fluids or the like and, more particularly, to a system that is capable of pumping or mixing a temperature sensitive fluid using a rotating magnetic element or bearing that levitates above a cold superconducting element.

BACKGROUND OF THE INVENTION

Most pharmaceutical solutions and suspensions manufactured on an industrial scale require highly controlled, thorough mixing to achieve a satisfactory yield and a uniform distribution of ingredients in the final product. Agitator tanks are frequently used to complete the mixing process, but a better degree of mixing is normally accomplished by using a mechanical stirrer or impeller (e.g., a set of mixing blades attached to a steel rod). Typically, the mechanical stirrer or impeller is simply lowered into the fluid through an opening in the top of the vessel and rotated by an external motor to create the desired mixing action.

One significant limitation or shortcoming of such an arrangement is the danger of contamination or leakage during mixing. The rod carrying the mixing blades or impeller is typically introduced into the vessel through a dynamic seal or bearing. This opening provides an opportunity for bacteria or other contaminants to enter, which of course can lead to the degradation of the product. A corresponding danger of environmental contamination exists in applications involving hazardous or toxic fluids, or suspensions of pathogenic organisms, since dynamic seals or bearings are prone to leakage. Cleanup and sterilization are also made difficult by the dynamic bearings or seals, since these structures typically include folds and crevices that are difficult to reach. Since these problems are faced by all manufacturers of sterile solutions, pharmaceuticals, or the like, the U.S. Food and Drug Administration (FDA) has consequently promulgated strict processing requirements for such fluids, and especially those slated for intravenous use.

Recently, there has also been an extraordinary increase in the use of biosynthetic pathways in the production of pharmaceutical materials, but problems plague those involved in this rapidly advancing industry. The primary problem is that suspensions of genetically altered bacterial cells frequently used to produce protein pharmaceuticals (insulin is a well-known example) require gentle mixing to circulate nutrients. If overly vigorous mixing or contact between the impeller and the vessel wall occurs, the resultant forces and shear stresses may damage or destroy a significant fraction of the cells, as well as protein molecules that are sensitive to shear stresses. This not only reduces the beneficial yield of the process, but also creates deleterious debris in the fluid suspension that requires further processing to remove.

In an effort to overcome this problem, others have proposed alternative mixing technologies. The most common proposal for stirring fluids under sterile conditions is to use a rotating, permanent magnet bar covered by an inert layer of TEFLON, glass, or the like. The magnetic bar is placed on the bottom of the agitator vessel and rotated by a driving magnet positioned externally to the vessel. Of course, the use of such an externally driven magnetic bar avoids the need for a dynamic bearing, seal or other opening in the vessel to transfer the rotational force from the driving magnet to the stirring magnet. Therefore, a completely enclosed system is provided. This of course prevents leakage and the potential for contamination created by hazardous materials (e.g., cytotoxic agents, solvents with low flash points, blood products, etc.), eases clean up, and allows for the desirable sterile interior environment to be maintained.

However, several well-recognized drawbacks are associated with this mixing technology, making it unacceptable for use in many applications. For example, the driving magnet produces not only torque on the stirring magnetic bar, but also an attractive axial thrust force tending to drive the bar into contact with the bottom wall of the vessel. This of course generates substantial friction at the interface between the bar and the bottom wall of the vessel. This uncontrolled friction generates unwanted heat and may also introduce an undesirable shear stress in the fluid. Consequently, fragile biological molecules, such as proteins and living cells that are highly sensitive to temperature and shear stress, are easily damaged during the mixing process, and the resultant debris may contaminate the product. Moreover, the magnetic bar stirrer does not generate the level of circulation provided by an impeller, and thus cannot be scaled up to provide effective mixing throughout the entire volume of large agitation tanks of the type preferred in commercial production operations.

In yet another effort to eliminate the need for dynamic bearings or shaft seals, some have proposed mixing vessels having external magnets that remotely couple the mixing impeller to a motor located externally to the vessel. A typical magnetic coupler consists of a drive magnet attached to the motor and a stirring magnet carrying an impeller. Similar to the magnetic bar technology described above, the driver and stirrer magnets are kept in close proximity to ensure that the coupling between the two is strong enough to provide sufficient torque. An example of one such proposal is found in U.S. Pat. No. 5,470,152 to Rains.

As described above, the high torque generated can drive the impeller into the walls of the vessel creating significant friction. By strategically positioning roller bearings inside the vessel, the effects of friction between the impeller and the vessel wall can be substantially reduced. Of course, high stresses at the interfaces between the ball bearings and the vessel wall or impeller assembly result in a grinding of the mixing proteins and living cells, and loss of yield. Further, the bearings are frequently sensitive to corrosive reactions with water-based solutions and other media and will eventually deteriorate, resulting in frictional losses which slow the impeller and reduce the mixing action and eventually also lead to undesirable contamination of the product. Bearings also add to the cleanup problems.

In an effort to address and overcome the limitations described above, still others have proposed levitated bearings designed to reduce the deleterious effects of friction resulting from magnetically coupled mixers. By using a specially configured magnetic coupler to maintain only a repulsive levitation force in the vertical direction, the large thrust force between the stirring and driving magnets can be eliminated, along with the resultant shear stress and frictional heating. An example of one such arrangement is shown in U.S. Pat. No. 5,478,149 to Quigg.

However, one limitation remaining from this approach is that only magnet-magnet interactions provide the levitation.

This leads to intrinsically unstable systems that produce the desired levitation in the vertical direction, but are unable to control side-to-side movement. As a result, external contact bearings in the form of bearing rings are necessary to laterally stabilize the impeller. Although this "partial" levitation reduces the friction between the impeller and the vessel walls, it does not totally eliminate the drawbacks of the magnetically coupled, roller bearing mixers previously mentioned.

In an effort to eliminate the need for contact or other types of mechanical roller bearings, complex feedback control has been proposed to stabilize the impeller. Typical arrangements use electromagnets positioned alongside the levitating magnet. However, the high power level required to attain only sub-millimeter separations between the levitating magnet and the stabilizing magnets constitutes a major disadvantage of this approach. Furthermore, this solution is quite complex, since the stabilizing magnets must be actively monitored and precisely controlled by complex computer-implemented software routines to achieve even a moderate degree of stability. As a consequence of this complexity and the associated maintenance expense, this ostensible solution has not been accepted in the commercial arena, and it is doubtful that it can be successfully scaled up for use in mixing industrial or commercial scale process volumes.

Still others have proposed the use of superconductive materials to levitate magnetic bearings. However, a significant limitation on the application of this technology to mixing systems results from the very cold temperatures required to create the desired superconductive effects. Even recently discovered "high temperature" superconductors often require temperatures on the order of 77 to 130 Kelvin to induce reliable, stable levitation in a magnetic bearing. In the past, the relatively wide separation distance required between the bearing, the cryostat outer wall, and the superconducting element to prevent unwanted cooling the fluid has limited the industrial applicability of this approach. To date, applications of this technology to fluids have been primarily in the pumping of cryogens or the like, such as those typically used in cold fusion experiments, in flywheels or other energy storage devices, or for space travel (see representative U.S. Pat. No. 5,747,426 to Abboud or U.S. Pat. No. 4,365,942 to Schmidt), where there is of course little concern for the inevitable cooling effect created.

In my prior U.S. Pat. No. 5,567,672, I describe a levitating magnetic "non-contact" bearing that is thermally separated from the superconducting element by the double-walled vacuum jacket of the cryostat used to cool the superconducting element. This thermal separation reduces the thermal transfer between the cold superconducting element and the levitating bearing as well as the fluid being mixed, so that it could possibly be used in mixing relatively temperature sensitive fluids, such as cell suspensions or blood. However, the resultant increased separation distance between the superconducting element and the bearing created by the double wall vacuum gap significantly decreases the stability and the load capacity of the bearing. This limits the applications in which this arrangement is useful, and especially precludes use with particularly viscous fluids or with the large volumes of fluid typically present in commercial scale operations.

Thus, a need is identified for an improved system having a levitating magnetic bearing for mixing or pumping fluids, and especially ultra-pure, hazardous, or delicate fluid solutions or suspensions. The system would preferably employ a magnetic bearing that carries an impeller and levitates in a stable fashion to avoid contact with the bottom or side walls of the vessel. Since the bearing would levitate in the fluid, no mixing rod or other structure penetrating the mixing vessel would be necessary, thus eliminating the need for dynamic bearings or seals and all potentially deleterious effects associated therewith. Since penetration is unnecessary, the vessel could be completely sealed prior to mixing to avoid the potential for contamination and reduce the potential for exposure in the case of hazardous or biological fluids, such as contaminated blood or the like. The vessel and magnetic bearing could also be made of disposable materials and discarded after each use, which would eliminate the need for cleaning or sterilization. The absence of a mixing or stirring rod penetrating through the vessel would also allow a slowly rotating impeller to be held at an off-axis position in a sealed vessel, thus making it possible to independently rotate the vessel about its central axis to achieve very gentle, yet thorough, mixing.

The use of superconductivity to provide the desired levitation would be possible by thermally isolating and separating the superconducting element from the magnetic bearing and providing a separate, substantially isolated cooling source. This combined thermal isolation and separation would avoid creating any significant cooling in the vessel, magnetic bearing or the fluid being mixed or pumped. Overall, the proposed system would have superior characteristics over existing mixing or pumping technologies in sterility, mixing quality, safety and reliability, and would be readily adaptable for use in larger, industrial scale operations.

SUMMARY OF THE INVENTION

Accordingly, keeping the above needs in focus, a primary object of the present invention is to provide a system for pumping or mixing a fluid using a levitating magnetic bearing that overcomes the shortcomings, limitations and disadvantages of the previously described prior art approaches.

Another object of the present invention is to provide a pumping or mixing system wherein a magnetic bearing is levitated in the fluid in a stable fashion by a superconducting element, thereby eliminating the need for dynamic seals or bearings in the vessel walls and the frictional heat and shear stress created through the use of magnetic bar stirrers or the like.

A related object of the present invention to provide a fluid pumping or mixing system wherein the superconducting element is thermally isolated from the levitating magnetic bearing, thereby allowing it to be placed in relatively close proximity to the vessel while avoiding the creation of any significant cooling in the fluid held therein.

A further object is to provide a mixing system wherein the vessel containing the levitating magnetic bearing can be completely sealed prior to mixing.

Yet another object of the invention is to provide a fluid pumping or mixing system wherein the rotating, levitating magnetic bearing is selectively movable to an off-axis position within a sealed vessel.

Yet a further object is to provide a vessel and levitating magnetic bearing that are both fabricated of disposable materials and can simply be discarded after mixing or pumping is completed to avoid the need for clean up and sterilization.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, a system that is capable of pumping or mixing temperature sensitive fluids using a magnetic pumping or mixing element, also referred to herein as a pumping or mixing structure or a bearing, levitated by a cold superconducting element is disclosed. The magnetic element/bearing, carries at least one impeller and is placed in a fluid vessel positioned externally to the outer wall of a cryostat or other housing for the superconducting element. A separate cooling source thermally linked to the superconducting element provides the necessary cooling to create the desired superconductive effects and induce levitation in the magnetic element, or bearing. In the preferred embodiment, the cryostat outer wall or other housing defines a chamber around the superconducting element that thermally isolates it from the vessel containing the magnetic element or bearing and the superconducting element. To minimize thermal transfer from the superconducting element contained in the chamber to the outer wall of housing, this chamber is evacuated or filled with an insulating material. This thermal isolation and separation means that the superconducting element can be placed in close proximity to the outer wall of the cryostat or other housing adjacent to the vessel to achieve a significant reduction in the separation distance between the levitating magnetic element, or bearing, and the superconducting element. This advantageously enhances the magnetic stiffness and loading capacity of the magnetic element/bearing as it levitates. However, since the superconducting element is thermally isolated from the wall or housing, the magnetic element/bearing, and hence the vessel and fluid contained therein, are not exposed to the cold temperatures required to generate the desired superconductive effects. By using means external to the vessel to rotate and stabilize the magnetic element/bearing levitating in the fluid, the desired pumping or mixing action is provided.

As should be appreciated from reviewing the foregoing description, several advantages are provided through the use of the mixing or pumping system of the present invention. Since the rotating magnetic bearing levitates in the fluid, there is no mechanical stirrer or mixing rod extending through any wall of the vessel, which means that the vessel can be completely sealed from the outside environment, if desired. This eliminates the need for a dynamic bearing or seal and the concomitant problems with leakage, sterility, and the like, which makes the present arrangement particularly well suited for use in pumping or mixing ultra-pure or hazardous fluids. Furthermore, exceptionally stable levitation is provided by the minimal separation distance between the superconducting element and the magnetic bearing, which is of course possible due to the thermal isolation and separation of the superconducting element from the outer wall of the cryostat. Contact-free, stable levitation reduces the incidence of frictional heating or unwanted shear stresses, both of which can have a significant deleterious effect on sensitive fluids, such as cell suspensions or the like.

In a preferred embodiment, the magnetic bearing includes first and second spaced permanent magnets mounted at the opposite ends of a support shaft that carries at least one impeller. The first magnet is placed in the fluid vessel closest to the outer wall of the cryostat such that it is levitated by the superconducting element. While those of skill in the art will understand that the polarity of the first permanent magnet is not critical for producing the desired levitation, it is preferred that it is disc-shaped and polarized in the vertical direction. This ensures that the magnetic field generated is substantially symmetrical and the desired stable levitation and free rotation relative to the vertical axis results.

The second permanent magnet is provided to form a magnetic coupling with the motive device for rotating the magnetic bearing, which is preferably a drive magnet rotated by a motor. In applications where the stability of the magnetic bearing is particularly important, the drive magnet includes more than one magnet, and in the most preferred embodiment has at least two sub-magnets that correspond to opposite polarity sub-magnets forming a part of the second permanent magnet. In addition to creating the desired magnetic coupling for transmitting the driving torque, these cooperating sub-magnets create an attractive force that balances with the levitational force produced by the superconducting element to keep the bearing properly balanced in the vertical direction. The cooperating sub-magnet pairs also keep the levitating bearing axially aligned and prevent side-to-side movement. In combination, the magnetic couplings created by the sub-magnet pairs allow the bearing to rotate in an exceptionally stable fashion. This reduces the chance of inadvertent contact between the bottom and side walls of the vessel, and eliminates the need for electromagnets, roller bearings, or like structures found in prior art pumps or mixers.

The superconducting element is preferably formed of melt-textured Yttrium-Barium Copper Oxide (YBCO), which is a well-known high temperature "type II" superconducting material, formed into a relatively thin pellet. The thermal link between the superconducting element and the cooling source is an elongate rod formed of a material having desirable thermal transfer characteristics. Metals, such as copper, brass, aluminum, or the like, are particularly well-suited for this purpose, but the use of any other material having good thermal conductance/low thermal resistance is possible. Preferably, the rod is cylindrical in shape such that one end has a relatively large surface area that fully contacts and engages an entire face of the superconducting element to maximize thermal transfer. While one end of the rod supports the superconducting element in the vacuum chamber defined by the outer wall of the cryostat or other housing, which remains at room temperature, the opposite end is kept in thermal contact with the cooling source. The cooling source may take the form of a separate cooling chamber in the cryostat holding a cryogen at a temperature between 4.2 and 130 Kelvin, and most preferably liquid nitrogen at a temperature between approximately 65–80 Kelvin. Instead of liquid cryogens, the use of alternate means for cooling the rod is possible, such as providing a separate closed cycle refrigerator is kept entirely outside of the cryostat or other housing for the superconducting element.

Since the magnetic bearing levitates without the need for a mixing rod or other form of driving shaft, it should be appreciated that the vessel containing the fluid may be completely sealed from the outside environment and used to mix, rather than pump, the fluid. By using such an arrangement, the potential for leakage or contamination during mixing is eliminated, as is the risk of human exposure to hazardous or biologically active fluids. Forming the sealed vessel and the magnetic bearing from disposable materials is also possible, such that they can simply be discarded after mixing is complete and the fluid is recovered, if necessary. This advantageously avoids the need for clean up or sterilization of the vessel and bearing.

Also, since there is no need for a dynamic bearing or seal for any drive shaft penetrating through a wall of the vessel, the vertical center axis of rotation of the magnetic bearing can be easily offset from the vertical center axis of the vessel. The vessel can then be rotated in a direction counterclockwise to the rotation of the bearing mounted in such an offset position. By doing so, gentle, yet thorough mixing may be provided in an efficient manner.

It should also be appreciated that other alternatives to a sealed vessel are also possible. Of course, the vessel may simply be open to the ambient environment, as may be desired during the mixing of some solutions or suspensions that require exposure to open air during mixing to achieve a desired result. Alternatively, the vessel may be substantially sealed with only an inlet and an outlet, such that the rotating impeller provides pumping action to move the fluid through the vessel. Manufacturing the open top or substantially sealed vessel of disposable materials is also possible, such that both the vessel and magnetic bearing can simply be discarded after use to avoid the need for clean up or sterilization.

A method of pumping or mixing a fluid in a vessel is also disclosed. The method includes the steps of placing a magnetic bearing carrying at least one impeller in the vessel. Levitation is induced in the magnetic bearing by a superconducting element positioned in a evacuated or insulated chamber defined by the outer wall of a cryostat or other housing. The chamber serves to thermally isolate and separate the vessel, fluid, and magnetic bearing from the superconducting element, which is thermally linked to a separate cooling source. Upon rotating the levitating magnetic bearing in the vessel, the desired mixing or pumping action is provided. As described above, the magnetic bearing and vessel may also be formed of disposable materials and discarded once mixing is complete and the fluid is recovered.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming apart of the specification illustrate several aspects of the present invention and, together with the description, serve to explain the principles of the invention. In the drawings.

Reference will now be made in detail to the present preferred embodiment of the invention, an example of which is illustrated in the accompanying drawing.

DETAILED DESCRIPTION OF THE INVENTION

Figure 1:
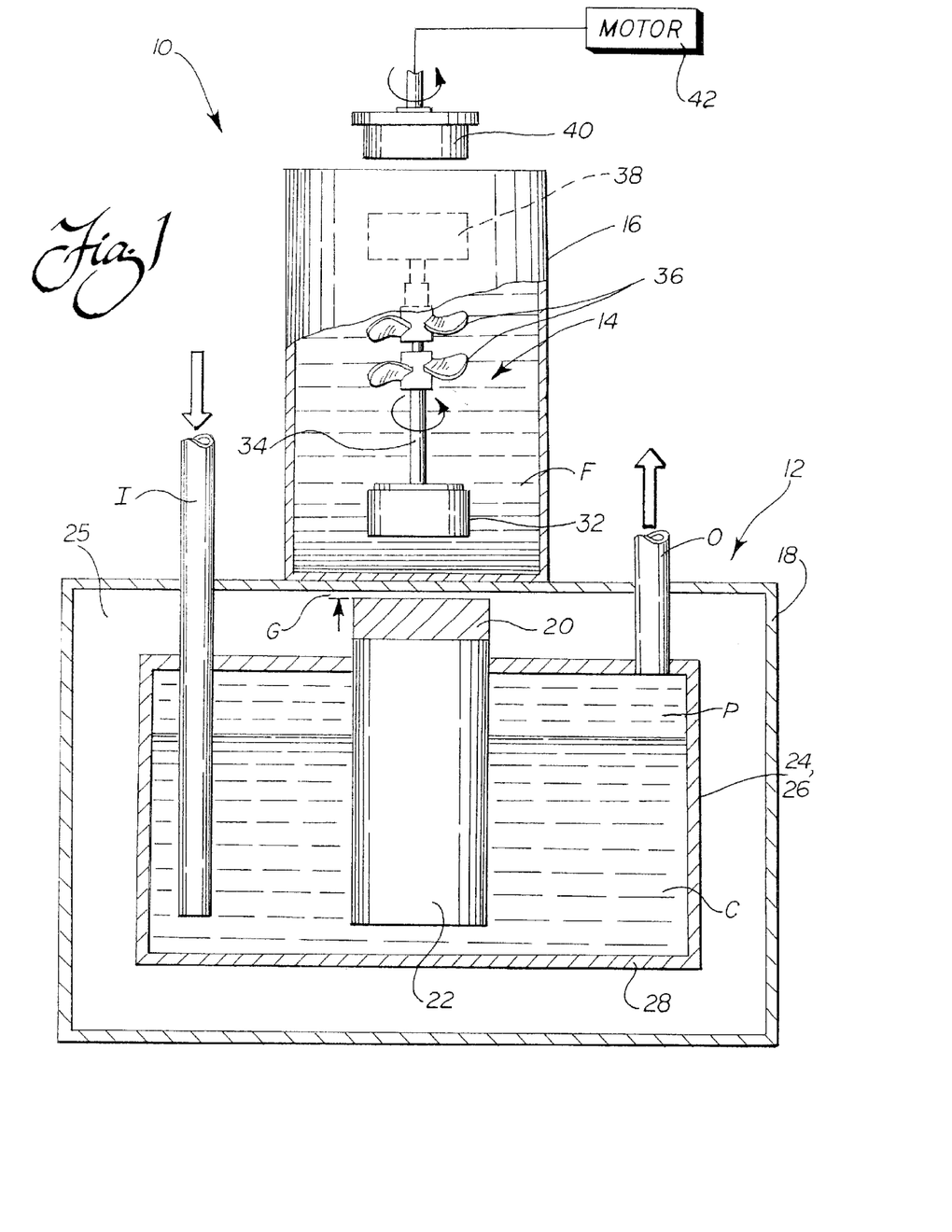
FIG. 1 is a partially cross-sectional, partially cutaway, partially schematic view of one embodiment of the system of the present invention wherein the levitating magnetic bearing is rotated by an external drive magnet to mix a fluid in a vessel and the cooling source is a separate cooling chamber in a cryostat holding a cryogen.
Figure 1A:
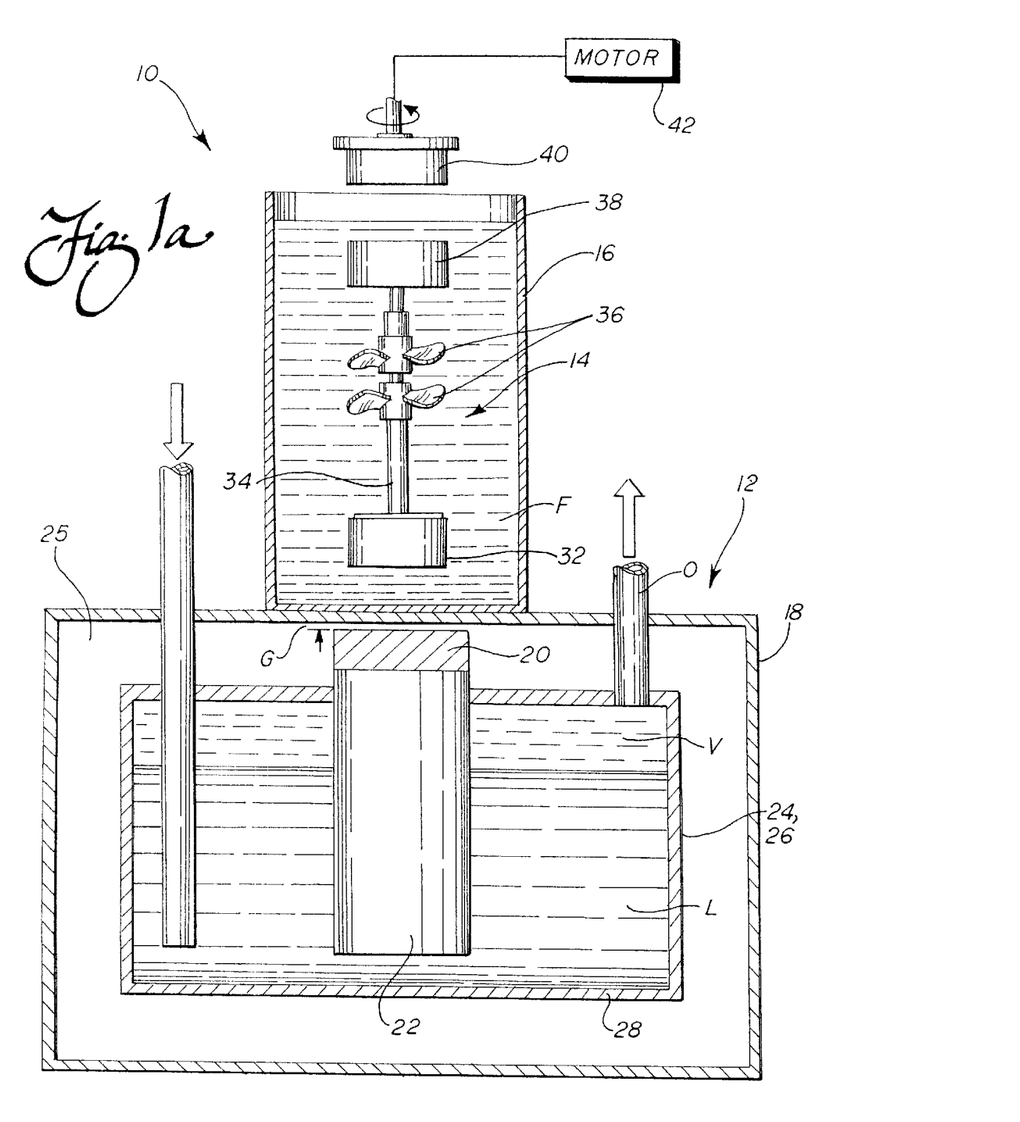
FIG. 1a is a partially cross-sectional, partially cutaway, partially schematic view of one embodiment of the system of the present invention wherein the levitating magnetic element or bearing is rotated by an external drive magnet to mix a fluid in a vessel having a sealable opening at the top and a closed bottom with no pre-defined outlet and the cooling source is a separate cooling chamber in a cryostat holding a cryogen.

Reference is now made to FIG. 1, which shows a first embodiment of the mixing or pumping system 10. In this embodiment, a cryostat 12 is used as the cooling source for the superconductor that produces the desired levitation in a magnetic pumping or mixing element 14, which is shown for purposes of illustration as a magnetic bearing 14. The magnetic element or bearing 14 is placed in a vessel 16 positioned external to the cryostat 12, which may already contain a fluid F or may be filled after the bearing is in place. The vessel 16 is shown as cylindrical in shape and may have an open top (see FIG. 1a). Alternatively, it may be completely sealed from the ambient environment to avoid the potential for fluid contamination or leakage during mixing, or adapted to pump the fluid F from an inlet to an outlet in the vessel 16 (see FIG. 2). In any case, the vessel 16 may be fabricated of any material suitable for containing fluids, including glass, plastic, metal, or the like. Of course, the use of lightweight plastic or other high density polymers is particularly desirable if the vessel 16 is going to be discarded after mixing or pumping is complete, as set forth in more detail in the description that follows.

As illustrated, the vessel 16 rests atop the outer wall 18 of the cryostat 12. Preferably, this outer wall 18 is fabricated of non-magnetic stainless steel, but the use of other materials is of course possible, as long as the ability of the magnetic bearing 14 to levitate remains substantially unaffected. Positioned inside of the wall 18 is a superconducting element 20, which is supported by a rod 22 that provides the thermal link between the superconducting element 20 and a separate cooling source 24. The outer wall 18 of the cryostat 12 defines a chamber 25 that is preferably evacuated to thermally isolate the cold superconducting element 20 from the relatively warm vessel 16, magnetic bearing 14, and fluid F. Positioning of the superconducting element 20 in this vacuum chamber 25 is possible by virtue of the thermal link provided by the rod 22. The thermal isolation and separation provided by the chamber 25 allows for the superconducting element 20 to be placed in very close proximity to the outer wall 18 without affecting the temperature of the outer wall 18 or vessel 16. This allows the separation distance from the superconducting element 20 to the inner surface of the wall 18 to be narrowed significantly, such that in the preferred embodiment, the gap G between the two is under 10 millimeters, and can be as narrow as approximately 0.01 millimeters. This substantial reduction in the separation distance enhances the levitational stability, magnetic stiffness, and loading capacity of the bearing 14 without the concomitant cooling effects associated with prior art approaches for levitating magnetic bearings above cold superconducting elements.

In the illustrated embodiment, the cooling source 24 is a separate, substantially contained cooling chamber 26 holding a cryogen C, such as liquid nitrogen. The chamber 26 is defined by an outer wall 28 that is substantially thermally separated from the outer wall 18 of the cryostat 12 to minimize heat transfer. An inlet I is provided through this wall 28 for introducing the cryogen into the cooling chamber 26. To permit any vapor V to escape from the chamber 26 as the cryogen C warms, an exhaust outlet O is also provided (see action arrows in FIG. 1 also designating the inlet and outlet). In the illustrated embodiment, the inlet I and outlet O lines may be welded in place to suspend the cooling chamber 26 in the cryostat 12, but the use of any other support means that minimizes thermal transfer between the cooling chamber 26 and the cryostat wall or other housing 18 is also possible.

The rod 22 serving as the thermal link between the cooling source 24 and the superconducting element 20 is cylindrical and extends through the outer wall 28 of the cooling chamber 26. The entire surface area of the superconducting element 20 should contact the upper surface of the cylindrical rod 22 to ensure that thermal transfer is maximized. The rod 22 is preferably formed of materials having low thermal resistance/high thermal conductance, such as brass, copper, or aluminum.

As should be appreciated from viewing FIG. 1, and as previously noted, the combination of the outer wall 18 and the inner cooling chamber 26 in this first embodiment defines the chamber 25 around the superconducting element 20. Preferably, this chamber 25 is evacuated to minimize heat transfer from the cooling chamber walls 28 and the superconducting element 20 to the outer wall 18 of the cryostat 12. The evacuation pressure is preferably at least $10^{-3}$ torr, and most preferably on the order of $10^{-5}$ torr, but of course may be varied depending upon the requirements of a particular application. The important factor is that thermal transfer from the cooling source 24, which in this case is the cooling chamber 26 holding a cryogen C, and the superconducting element 20 to the outer wall 18 is minimized to avoid cooling the vessel 16 or fluid F held therein. Although a vacuum chamber 25 is presently proposed as one preferred manner of minimizing this thermal transfer, the use of other means to provide the desired thermal isolation is possible, such as by placing insulating materials or the like in the chamber 25.

As is known in the art, by cooling the superconducting element 20 in the presence of a magnetic field, it becomes capable of distributing the current induced by a permanent magnet such that the magnet levitates a certain distance above the superconducting element, depending primarily upon the intensity and the direction of the magnetic field generated by the levitating magnet. Although basically a repulsive force is created, the peculiar nature of the pinning forces generated actually tie the levitating magnet to the superconducting element as if the two were connected by an invisible spring. As should be appreciated, this form of attachment cannot be achieved in conventional levitation schemes for magnetic bearings that employ two opposed permanent magnets, since no pinning forces act to tie the two magnets together, while at the same time a balancing repulsive force is provided.

In the preferred embodiment of the present system 10, the element 20 providing the superconductive effects is a "high temperature type II" superconductor. Most preferably, the superconducting element 20 is formed of a relatively thin cylindrical pellet of melt-textured Yttrium-Barium Copper Oxide that, upon being cooled to a temperature of approximately 77–78 Kelvin using a cooling source 24, such as the illustrated liquid nitrogen chamber 26, exhibits the desired levitational properties in a permanent magnet. Of course, the use of other known superconducting materials having higher or lower operating temperatures is also possible, and my prior U.S. Pat. No. 5,567,672 is incorporated herein by reference for, among other things, the other high-temperature superconducting materials referenced therein.

The magnetic bearing 14 in the preferred embodiment includes a first permanent magnet 32 for positioning in the vessel 16 adjacent to the superconducting element 20 such that it levitates in the fluid F. Although the polarity of this first magnet 32 is not critical to creating the desired levitation, the magnet 32 is preferably disc-shaped and polarized in the vertical direction. This ensures that a symmetrical magnetic field is created by the magnet 32 and stable levitation results above the superconducting element 20 while free rotation relative to the vertical axis is possible.

In a version of the magnetic bearing 14 particularly adapted for use in relatively deep fluid vessels, a support shaft 34 is connected to and extends vertically from the first permanent magnet 32. Along the shaft 34, at least one, and preferably two, impellers 36 are carried that serve to provide the desired pumping, or in the case of FIG. 1, mixing action when the magnetic bearing 14 is rotated. Rotation of the levitating magnetic bearing 14 in the vessel 16 is achieved by a magnetic coupling formed between a second permanent magnet 38 (shown in dashed line outline in FIG. 1, but see also FIG. 2) and a drive magnet 40 positioned externally of the vessel 16. The drive magnet 40 is rotated by a drive means, such as an electric motor 42 or the like, and the magnetic coupling formed with the second permanent magnet 38 serves to transmit the driving torque to the bearing 14 to provide the desired pumping or mixing action. The direction of rotation is indicated by the action arrows shown in FIGS. 1 and 2 as being in the counterclockwise direction, but it should be appreciated that this direction is easily reversed by simply reversing the direction in which the drive magnet 40 is rotated.

In operation, and in practicing the method of pumping or mixing a fluid disclosed herein, the vessel 16 containing the fluid F and magnetic bearing 14 are together placed external to the wall 18 of the cryostat 12 adjacent to the superconducting element 20, which is placed in the chamber 25. When the first disc-shaped permanent magnet 32 is brought into the proximity of the superconducting element 20, the symmetrical magnetic field generated thereby causes the entire bearing 14 to levitate in a stable fashion above the bottom wall of the vessel 16. This levitation brings the second permanent magnet 38 into engagement with the drive magnet 40 to form the desired magnetic coupling. In addition to transmitting the driving torque, this magnetic coupling also serves to stabilize rotation of the magnetic bearing 14. The motor 42 or other motive device is then engaged to cause the drive magnet 40 to rotate, which in turn induces a steady, stable rotation in the bearing 14. Rotating impellers 36 then serve to mix or pump the fluid F in a gentle, yet thorough fashion.

Since the bearing 14 fully levitates and can be completely submerged in the fluid, the need for mixing or stirring rods penetrating through the vessel 16 is eliminated. The concomitant need for dynamic shaft seals or support bearings in the vessel walls is also eliminated. A related advantage is that the vessel 16 containing the fluid F and the magnetic bearing 14 can be completely sealed from the outside environment before mixing to provide further assurances against leakage or contamination. Yet another related advantage discussed in detail below is that the vessel 16 and magnetic bearing 14 can be formed of relatively inexpensive, disposable materials and simply discarded once mixing is complete. As should be appreciated, this advantageously eliminates the need for cleanup and sterilization of the magnetic bearing 14 and vessel 16. Thus, by completely sealing a disposable vessel containing a magnetic bearing and a fluid prior to mixing, the entire assembly can simply be discarded once the fluid contents are recovered, thereby reducing the risk of human exposure both during and after mixing in the case of hazardous fluids.

Figure 2:
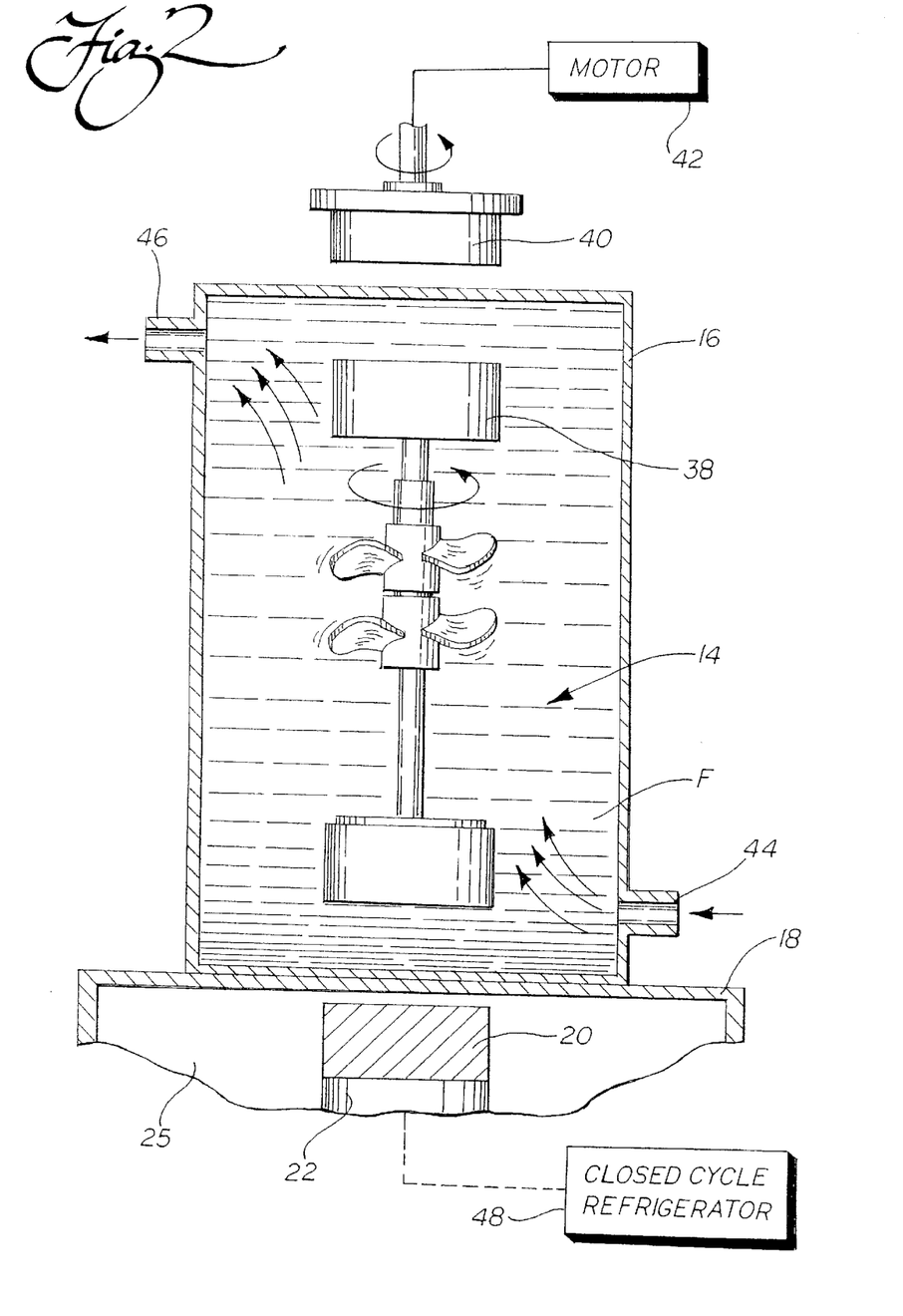
FIG. 2 is an enlarged cross-sectional, partially cutaway, partially schematic view of a second embodiment wherein the rotating, levitating magnetic bearing is used to pump a fluid through a vessel resting atop a housing for the superconducting element and the cooling source is a closed cycle refrigerator.

A second embodiment of the system 10 of the present invention particularly adapted for pumping a fluid F is shown in FIG. 2. In this embodiment, the vessel 16 includes at least one fluid inlet 44 and at least one outlet 46. The rotating impellers 36 serve to provide the desired pumping action by forcing fluid F from the inlet 44 to the outlet 46 (see action arrows). By increasing or decreasing the rotational speed of the motor 42 or other motive device, or adjusting the size, shape or style of the impeller blades, or substituting a different design altogether, a precise level of pumping action may be provided.

Another possible modification shown in FIG. 2 is to use a closed cycle refrigerator 48 to provide the necessary cooling for the superconducting element 20 instead of a cryostat with a liquid cryogen. The refrigerator 48 can be positioned externally to a housing 18 containing the superconducting element 20, which may be the equivalent of the cryostat outer wall 18 previously described. As with the first embodiment, a chamber 25 is defined by the housing 18. This chamber 25 is preferably evacuated or filled with other insulating materials to minimize thermal transfer from the superconducting element 20 to the housing 18. However, since no cooling source 24 is contained within the housing 18, it is not actually a "cryostat" as that term is commonly defined. Nevertheless, the desired dual levels of thermal separation are still possible, and the concomitant advantages provided, since: (1) the cooling source 24, 48 is positioned away from the housing 18 and, thus, the vessel 16, magnetic bearing 14, and fluid F; and (2) the housing 18 still separates and defines a chamber 25 that thermally isolates the superconducting element 20 and the vessel 16. In yet another alternate arrangement, the refrigerator 48 can be used as a primary cooling source, with the cryogenic chamber 26 provided as a secondary or "backup" cooling source in the event of a power outage or mechanical failure (not shown).

Figure 3:
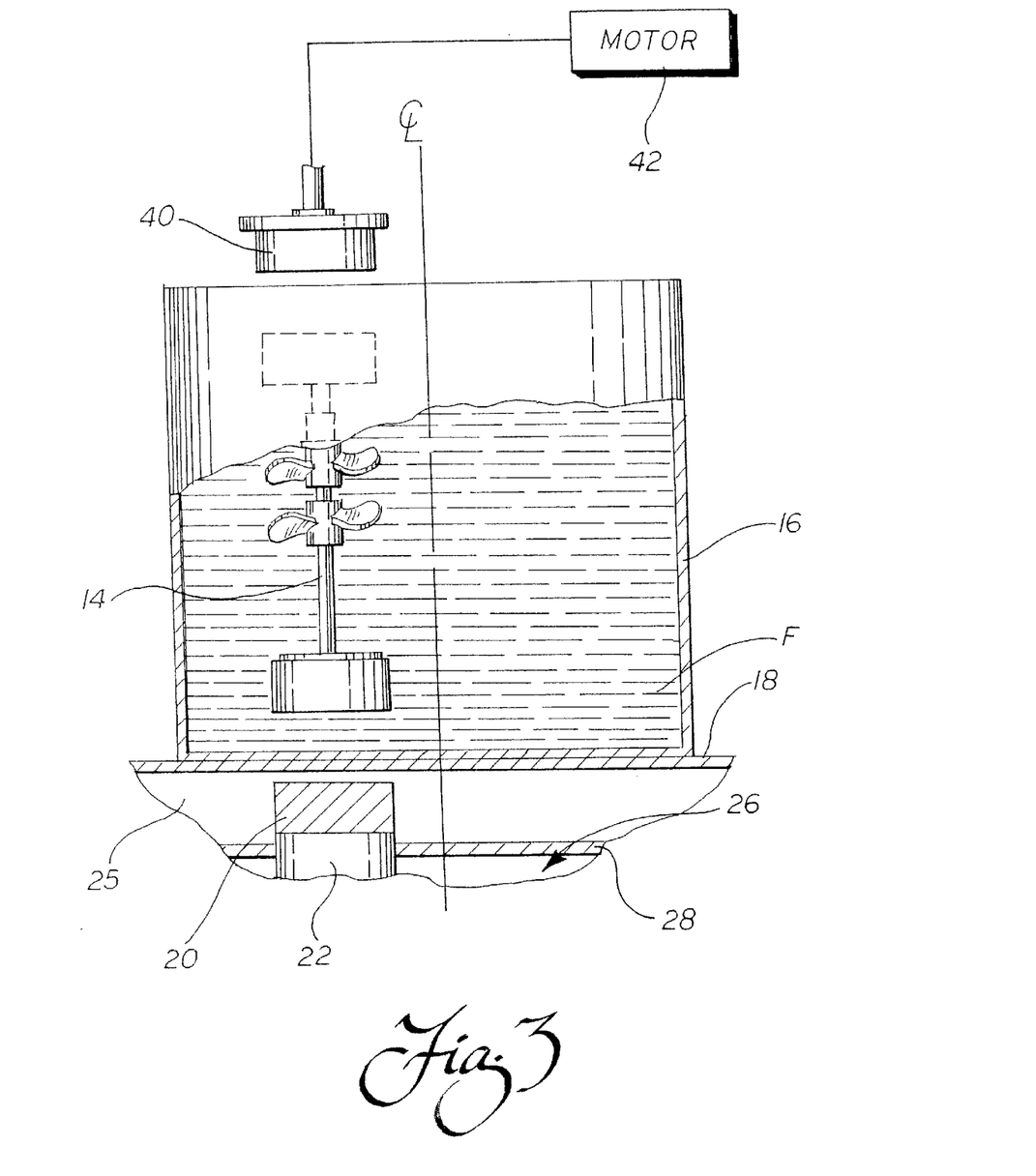
FIG. 3 is a partially cross-sectional, partially cutaway, partially schematic view of the system of the first embodiment wherein the superconducting element, vessel, magnetic bearing, and drive magnet are axially aligned, but moved off-center relative to the vertical center axis of the vessel.

In accordance with another of the many important aspects of the present system 10, the absence of a mixing rod or other mechanical stirrer extending through a wall of the vessel 16 also allows for placement of the magnetic bearing 14 at an off-axis position, as shown in FIG. 3. Specifically, the superconducting element 20, magnetic bearing 14, and drive magnet 40 are all axially aligned away from the vertical center axis of the vessel 16. One particular advantage of using this approach is that the magnetic bearing 14 may be rotated at a very low speed while the vessel 16 is also rotated about its center axis. This advantageously ensures that gentle, yet thorough mixing, is achieved, which is particularly advantageous for use with fluids that are sensitive to shear stress. As should be appreciated, this arrangement can be used both whether the vessel 16 is completely sealed, provided with an inlet 44 and an outlet 46 for pumping as shown in FIG. 2, or open to the ambient environment. For purposes of illustration only, FIG. 3 shows the cryostat 12 of the embodiment shown in FIG. 1 having an outer wall 18 and a cooling chamber 26 defined by a wall 28. However, it should be appreciated that use of the housing 18 and closed-cycle refrigerator 48 of the second embodiment of FIG. 2 as the "cryostat" is also possible with this arrangement.

Figure 4A:
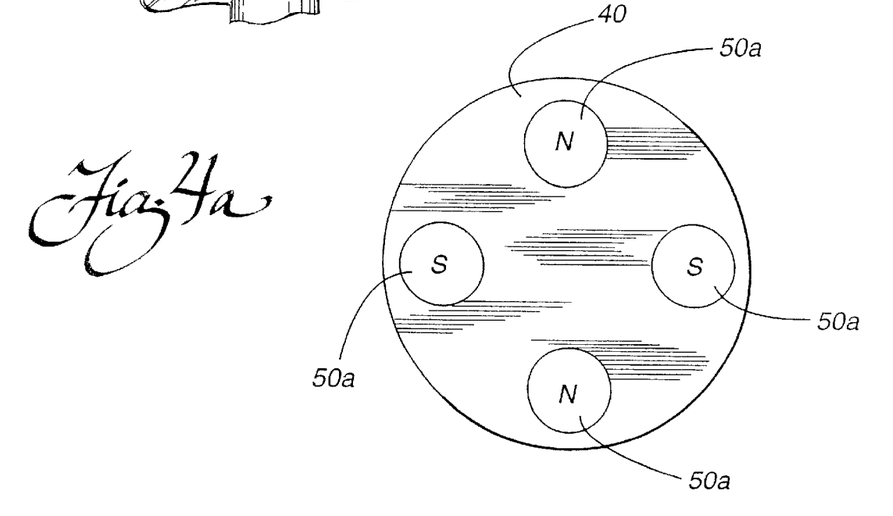
FIG. 4a is a bottom view of the drive magnet used in situations where exceptional rotational stability of the magnetic bearing of the preferred embodiment is required.
Figure 4B:
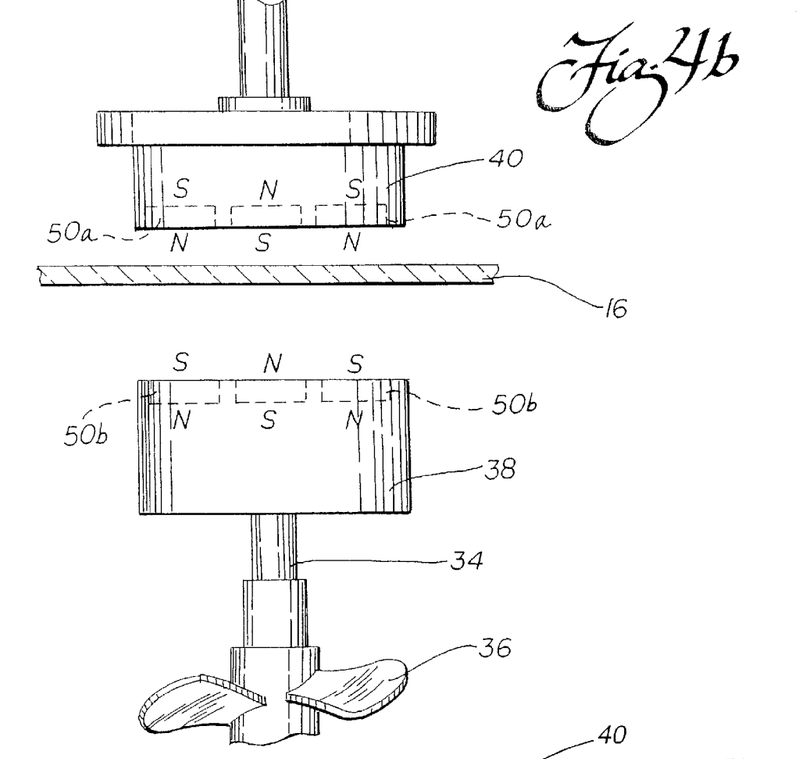
FIG. 4b is a partially cross-sectional, partially cutaway side view of the system showing the drive magnet of FIG. 4a magnetically coupled to a similarly constructed second permanent magnet forming a part of the magnetic bearing.

Through experimentation, it has been discovered that when the magnetic bearing 14 of the type described for use in the preferred embodiment is employed, providing the requisite degree of stability to ensure that all contact with the side walls of the container 16 is avoided can be a concern. Thus, to ensure that the magnetic bearing 14 rotates with exceptional stability and such contact is completely avoided, the second permanent magnet 38 and the drive magnet 40 are each provided with at least two pair, and preferably four pair of cooperating sub-magnets 50a, 50b. As shown in FIGS. 4a and 4b, these magnets 50a, 50b preferably have opposite polarities and thereby serve to attract each other and prevent the levitating magnetic bearing 14 from making any substantial side-to-side movement. However, the attractive force is counterbalanced by the combined spring like attractive and repulsive levitational forces created between the first permanent magnet 32 and the superconducting element 20 when cooled. This avoids the potential for contact with the upper wall of the vessel 16, if present. Overall, the magnetic bearing 14 is capable of exceptionally stable rotation using this arrangement, which further guards against the undesirable frictional heating or shear stress created if the rotating bearing 14, or more particularly, the first and second permanent magnets 32, 38 or the blades of the impeller(s) 36 could move into close proximity with the bottom or side walls of the vessel 16.

As previously mentioned, one of the many advantages of the system 10 of the present invention is that, since the magnetic bearing 14 levitates in the fluid F and no mixing or stirring rods are required for rotation, the vessel 16 can be completely sealed from the outside ambient environment. Thus, by forming the bearing 14 and vessel 16 of relatively inexpensive or disposable materials, both can simply be discarded after mixing is completed and the fluid F is recovered. Of course, such disposable materials can also be used to form the vessel 16 designed for pumping fluids (FIG. 2), or to form the open-top container for mixing fluids, to avoid the need for clean up or sterilization once the operation is complete.

It should also be appreciated that the magnetic bearing 14 illustrated is a preferred arrangement only, and that other possible configurations are possible. For instance, impeller blades could simply be placed circumferentially around the disc-shaped first permanent magnet 32 to reduce the length of the shaft 34, or eliminate it altogether, if the vessel 16 is relatively short in the vertical dimension. Instead of a bladed impeller 36, the use of other structural arrangements is also possible, such as disc-shaped wheels having vanes or like structures designed to create the desired mixing or pumping action when rotated. Depending on the depth of the vessel 16, the length of the shaft 34, if present, can also be increased or decreased as necessary. All components forming the magnetic bearing in any embodiment described above may be coated with TEFLON or other inert materials to reduce the chances of contamination or corrosion, as well as to facilitate clean up, if required.

Of course, besides use in the mixing or pumping of small batches of fluid solutions or suspensions used during experimentation and research in the laboratory setting, all components are also easily scaled up for use in industrial or commercial pumping or mixing operations, such as those commonly used in the manufacture of pharmaceuticals on a large-scale basis. The levitation of the magnetic bearing can still be readily achieved in systems of much greater capacity than the one shown for purposes of illustration in the drawings, thus making the present arrangement particularly well-suited for the commercial production of pharmaceuticals or any other solutions or suspensions that require gentle, yet thorough mixing during processing.

Experiments conducted to date have demonstrated the efficacy of the system 10 described above as the most preferred embodiment. The set-up utilized in conducting these experiments included a magnetic bearing having axially aligned upper and lower magnets and an impeller mounted on a vertically extending support shaft, as shown in FIG. 1. A cylindrical pellet of melt-textured $YBa_2Cu_3O_{7+x}$ having a diameter of 30 millimeters and a thickness of 25 millimeters was used as the superconducting element and placed in a cryostat having a configuration similar to the one shown in FIG. 1. The cryostat included a cooling chamber filled with approximately 1 liter of liquid nitrogen. A Nd—Fe—B permanent magnet with a surface field intensity of 0.4 Tesla was used as the lower, first permanent magnet.

Experiments conducted using this set-up demonstrated that the desired exceptionally stable levitation of the magnetic bearing above the top surface of the cryostat in a vessel filled with a relatively warm fluid was possible. A separation distance of up to seven millimeters was achieved, and the levitation was stable for up to five hours using just a liter of liquid nitrogen as the cryogen. In the first experiment using this set up, water was selected as a model low viscosity fluid. Rotational speeds of up to 600 rpm were achieved—this upper limit being defined by only the limited capabilities of the motor used to rotate the drive magnet in this experiment. No decoupling or instability in the magnetic bearing was observed at any speed. In the case of glycerin, a model high viscosity fluid, a maximum rotational speed of 60 rpm was achieved before some decoupling of the magnetic bearing was observed. To further demonstrate the mixing capabilities using the proposed system, SEPHADEX powder (dry bead, 50–150 micron diameter) was placed on the bottom of a water-filled vessel and the levitating magnetic bearing rotated. A uniform suspension was achieved after approximately five minutes of mixing.

In summary, a system 10 using cold superconducting technology that is capable of pumping or mixing a relatively warm or otherwise temperature sensitive fluid using a levitating magnetic bearing 14 is disclosed. The magnetic bearing 14 carries at least one impeller 36 and is placed in a fluid vessel 16 positioned external to a cryostat 12 having an outer wall or other housing 18 for containing a superconducting element 20. A separate cooling source 24 (either a cryogenic chamber 26, FIGS. 1 and 3 or a refrigerator 48, FIG. 2) thermally linked to the superconducting element 20 provides the necessary cooling to create the desired superconductive effects and induce levitation in the magnetic bearing 14. Since the bearing levitates in the fluid F, no penetration of the vessel walls by mixing or stirring rods is necessary, which eliminates the need for dynamic bearings or seals. Additionally, the outer wall 18 of the cryostat 12 or other housing defines a chamber 25 that thermally isolates and separates the superconducting element 20 from the vessel 16 containing the fluid F and magnetic bearing 14. The thermal isolation may be provided by evacuating the chamber 25, or filling it with an insulating material. By virtue of this thermal isolation and separation, the superconducting element 20 can be positioned in close proximity to the outer wall or housing 18 adjacent to the vessel 16 and magnetic bearing 14, thereby achieving a significant reduction in the separation distance or gap G between the magnetic bearing 14 and the superconducting element 20. This enhances the magnetic stiffness and loading capacity of the magnetic levitating bearing 14, thus making it suitable for use with viscous fluids or relatively large volumes of fluid. The exceptionally stable levitation provided as a result of the reduced separation distance also significantly reduces the potential for contact between the rotating bearing and the bottom or sidewalls of the vessel, which makes this arrangement particularly well-suited for use in fluids that are sensitive to shear stress or the effects of frictional heating. However, since the superconducting element 20 is substantially thermally isolated and separated from the vessel 16, the magnetic bearing 14, and hence the fluid F contained therein, are not exposed to the cold temperatures generated by the cooling source 24 to produce the desired superconductive effects and the resultant levitation. This allows for temperature sensitive fluids to be mixed or pumped. By using means external to the vessel 16 to rotate and/or stabilize the magnetic bearing 14 levitating in the fluid F, such as a rotating drive magnet 40 magnetically coupled to the magnetic bearing 14, the desired pumping or mixing action is provided.

The foregoing description of a preferred embodiment of the present invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A system for pumping or mixing a fluid in a vessel, comprising:
    a magnetic element for placement in the vessel;
    a superconducting element for levitating said magnetic element;
    a wall defining a chamber around the superconducting element, said chamber thermally isolating the superconduction element from the vessel;
    a cooling source thermally linked to said superconducting element;
    a motive device for rotating said magnetic element,
    whereby the fluid is pumped or mixed by the rotation of the magnetic element.

2. The system for pumping or mixing a fluid according to claim 1, wherein a vacuum is maintained in the chamber around said superconducting element to minimize thermal transfer to said wall and provide the desired thermal isolation.

3. The system for pumping or mixing a fluid according to claim 2, wherein said vacuum is at least $10^{-3}$ torr.

4. The system for pumping or mixing a fluid according to claim 1, wherein said superconducting element is a high temperature superconducting element.

5. The system for pumping or mixing a fluid according to claim 4, wherein said high temperature superconducting element is fabricated of melt-textured Yttrium-Barium Copper Oxide (YBCO).

6. The system for pumping or mixing a fluid according to claim 1, wherein said cooling source is kept at a temperature of between 4.2 to 130 Kelvin.

7. The system for pumping or mixing a fluid according to claim 6, wherein said cooling source is kept at a temperature of between approximately 77 to 78 Kelvin.

8. The system for pumping or mixing a fluid according to claim 1, wherein said wall is the outer wall of a cryostat and said cooling source is a chamber in said cryostat holding liquid nitrogen.

9. The system for pumping or mixing a fluid according to claim 1, wherein said cooling source is a refrigerator.

10. The system for pumping or mixing a fluid according to claim 1, wherein said thermal link is provided by a rod extending between said superconducting element and said cooling source.

11. The system for pumping or mixing a fluid according to claim 1, wherein said levitating magnetic element is a magnetic bearing that further includes a first permanent magnet positioned adjacent to said superconducting element but external to said wall.

12. The system for pumping or mixing a fluid according to claim 11, wherein said first permanent magnet is disc shaped and polarized in the vertical direction to produce a symmetrical magnetic field.

13. The system for pumping or mixing a fluid according to claim 11, wherein said magnetic bearing further includes a second permanent magnet spaced from said first permanent magnet for forming a magnetic coupling with a drive magnet forming a part of said motive device, whereby said magnetic coupling serves to both transmit driving torque from said drive magnet to said magnetic bearing and stabilize the levitation of said magnetic bearing.

14. The system for pumping or mixing a fluid according to claim 13, wherein said magnetic bearing further includes at least one impeller mounted on a shaft extending substantially vertically between said first and second permanent magnets.

15. The system for pumping or mixing a fluid according to claim 13, wherein said motive device for said magnetic bearing includes a motor for rotating said drive magnet.

16. The system for pumping or mixing a fluid according to claim 13, wherein said second permanent magnet includes at least two submagnets that correspond to opposite polarity forming a part of said drive magnet, whereby said cooperating submagnets serve to stabilize said magnetic bearing during rotation.

17. The system for pumping or mixing a fluid according to claim 1, wherein said wall is below said magnetic element and the vessel rests atop said wall.

18. The system for pumping or mixing a fluid according to claim 1, wherein a gap is provided between said superconducting element and an inner surface of said wall of approximately 0.01 to 5 millimeters.

19. The system for pumping or mixing a fluid according to claim 1, wherein the vessel includes an inlet and an outlet, and further including at least one impeller associated with said magnetic element that creates an enhanced pumping action that forces fluid to move from said inlet to said outlet.

20. The system for pumping or mixing a fluid according to claim 1, wherein said vessel is completely sealed and said magnetic element serves to mix the fluid only.

21. The system for pumping or mixing a fluid according to claim 1, wherein the vertical center axis of rotation of the magnetic element is offset from the vertical center axis of the vessel.

22. A system for mixing a fluid, comprising:
a vessel for holding the fluid;
a magnetic element positioned in said vessel;
a superconducting element;
a housing defining a chamber around said superconducting element for thermally isolating said superconducting element from said vessel;
a cooling source thermally linked to said superconducting element; and
a motive device to rotate said magnetic element,
whereby the superconducting element is positioned adjacent to the vessel for levitating the magnetic element in the vessel and the rotation of the magnetic element creates the mixing action in the fluid.

23. The mixing system according to claim 22, wherein said chamber surrounding said superconducting element is evacuated to minimize thermal transfer to said housing and provide the desired thermal isolation.

24. The mixing system according to claim 22, wherein said vessel includes an inlet and an outlet, and said magnetic element includes at least one impeller that creates an enhanced pumping action that forces fluid to move from said inlet to said outlet.

25. The mixing system according to claim 22, wherein said vessel is completely sealed from the outside environment.

26. The mixing system according to claim 25, wherein said vessel and magnetic element are disposable.

27. A method of levitating and rotating and rotating a magnetic element in a vessel for the intended use of pumping or mixing at least a fluid, including a non-cryogenic fluid comprising:
placing the magnetic element in the vessel;
levitating the magnetic element in the vessel using a superconducting element positioned in an evacuated or insulated chamber and thermally linked to a cooling source; and
rotating the magnetic element in the vessel.

28. The method according to claim 27, further including the steps of placing said magnetic element in the vessel prior to introducing a fluid.

29. The method according to claim 27, including the step of completely sealing the vessel prior to rotating said magnetic element.

30. The method according to claim 27, further including the step of disposing of said magnetic element and/or said vessel when pumping or mixing is complete.

31. The method according to claim 27, further including the step of reusing the magnetic element and/or said vessel when pumping or mixing is complete.

32. An assembly for holding a fluid in a mixing system wherein a superconducting element levitates a mixing element and a motive device rotates the mixing element, comprising:
a sealed vessel capable of holding the fluid;
wherein the mixing element includes a magnet and is positioned in said sealed vessel such that it is capable of levitating in a non-contact fashion relative to the vessel in the absence of the fluid,
whereby said magnetic mixing element may be levitated in the vessel by the superconducting element and rotated by the motive device without the need for a shaft penetrating into the vessel and may be disposed of along with the vessel or reused when the mixing operation is complete.

33. The assembly according to claim 32, wherein the fluid is introduced into the vessel prior to sealing.

34. The assembly according to claim 32, wherein the fluid is introduced into the vessel after sealing.

35. A method of pumping or mixing a fluid, comprising:
placing a pumping or mixing element in a vessel and sealing the vessel;
levitating the magnetic element in the vessel using a superconducting element placed in a superconducting state in accordance with a field cooling protocol;
introducing the fluid into the vessel;
rotating the magnetic element,
whereby the active rotation of the levitating, magnetic pumping or mixing element serves to pump or mix the fluid in the vessel when present.

36. The method according to claim 35, wherein the vessel is formed of a disposable material, and further including the step of disposing of the vessel after at least a portion of the fluid is retrieved.

37. The method according to claim 35, wherein the step of levitating the pumping or mixing element includes positioning the superconducting element in an evacuated or insulated chamber and thermally linking the superconducting element to a cooling source.

38. The method according to claim 35, wherein the pumping or mixing element is a magnetic bearing including a levitation magnet for positioning adjacent to the superconducting element and at least two alternating polarity submagnets, and wherein the step of rotating the superconducting element includes positioning a motive device including a drive magnet structure adjacent to the vessel to form a magnetic coupling with the submagnets.

39. A system for pumping or mixing a fluid in a vessel, comprising:
a pumping or mixing structure for placement in the vessel, said pumping or mixing structure comprising first and second magnets and a support for supporting the magnets in a spaced configuration;
a superconducting element positioned adjacent to the vessel and the first magnet for levitating the pumping or mixing structure in the vessel;
a cryostat including a chamber for thermally isolating the superconducting element from the vessel;
a cooling source thermally linked to said superconducting element;
a motive device comprising one or more drive magnets for forming a magnetic coupling with the second magnet and rotating said magnetic pumping or mixing structure,
whereby the fluid is pumped or mixed by the rotation of the pumping or mixing structure.

40. The system according to claim 39, wherein the pumping or mixing structure further comprises at least one impeller or vane for enhancing the pumping or mixing action provided.

41. A system for pumping or mixing a fluid in a vessel, comprising:
a pumping or mixing structure for placement in the vessel, said pumping or mixing structure comprising a shaft carrying a levitation magnet at one end, at least one pair of alternating polarity driven magnets at the opposite end, and at least one impeller;
a superconducting element positioned adjacent to the vessel and the levitation magnet for levitating the pumping or mixing structure in the vessel;
a cryostat for thermally isolating the superconducting element from the vessel;
a cooling source thermally linked to the superconducting element;
a motive device including a motor for rotating a pair of alternating polarity driving magnets that form a magnetic coupling with the at least one pair of alternating polarity driven magnets,
whereby the rotation of the driving magnets serves to rotate the pumping or mixing structure via the magnetic coupling with the driven magnets.

42. The system according to claim 41, wherein the pumping or mixing structure comprises two pair of alternating polarity driven magnets and the motive device includes two pair of alternating polarity driving magnets.

43. A system for pumping or mixing a fluid, comprising:
a vessel having a first portion and a second portion;
a pumping or mixing structure for placement in the vessel, said pumping or mixing structure comprising a levitation magnet structure positioned adjacent to a first portion of the vessel and a driven magnet structure positioned adjacent to the second portion of the vessel;
a superconducting element positioned adjacent to the vessel and the levitation magnet structure for levitating the pumping or mixing structure;
a motive device including a motor for rotating one or more driving magnets that form a magnetic coupling with the driven magnet structure of said pumping or mixing structure;
a cryostat including a wall for supporting the vessel and defining a chamber for thermally isolating the superconducting element from the vessel and a cooling source thermally linked to the superconducting element in the chamber;
whereby the rotation of the driving magnet serves to rotate the pumping or mixing structure via the magnetic coupling.

44. The system according to claim 43, wherein the first and second portions of the vessel are spaced in a vertical direction.

45. A system for pumping or mixing a fluid in a vessel, comprising:
a pumping or mixing structure for placement in the vessel, said pumping or mixing structure comprising a shaft carrying a first magnet at one end, at least one pair of alternating polarity driven magnets at the opposite end, and at least one impeller;
a superconducting element positioned adjacent to the vessel and the first magnet for levitating the pumping or mixing structure in the vessel;
a cryostat including a wall defining a chamber for thermally isolating the superconducting element from the vessel and a cooling source thermally linked to the superconducting element in the chamber;
a motive device including a motor for rotating a pair of alternating polarity driving magnets that form a magnetic coupling with the at least one pair of alternating polarity driven magnets,
whereby the rotation of the driving magnets serves to rotate the pumping or mixing structure via the magnetic coupling with the driven magnets.

46. An assembly for holding a fluid for intended use in a pumping or mixing system having a levitation device that levitates a pumping or mixing structure and a motive device including a driving magnet structure rotates the pumping or mixing structure, comprising:

a vessel capable of holding the fluid;

wherein the pumping or mixing structure comprises a shaft carrying a first magnet at one end, at least one pair of alternating polarity driven magnets at the opposite end, and at least one impeller;

whereby the first magnet of said pumping or mixing structure may be levitated in the vessel in a non-contact fashion by the levitation device and the alternating polarity driven magnets may be rotated by driving magnet of the motive device, both without the need for a shaft penetrating into the vessel.

47. The assembly according to claim 46, wherein the vessel is formed of a disposable material.

48. The assembly according to claim 46, wherein the vessel is sealed after the pumping or mixing element is positioned therein.

49. The assembly according to claim 46, wherein the vessel is unsealed prior to use to introduce a fluid therein.

50. The assembly according to claim 46, wherein the vessel is selected from the group consisting of an open-top container, a container having an inlet and an outlet, and a sealed container.

51. A structure for intended use in mixing a fluid using a system wherein a superconducting element levitates a mixing element and a motive device rotates the mixing element, comprising:

a mixing vessel for holding the fluid during mixing, said vessel having a sealable opening, no pre-defined outlet, and a substantially planar bottom surface;

wherein the mixing element includes a levitation magnet and is positioned in the vessel such that it is capable of levitating in a non-contact fashion substantially and entirely above the planar bottom surface in the absence of a fluid;

whereby the mixing element may be levitated in the vessel by the superconducting element and rotated by the motive device without the need for a shaft penetrating into the vessel and may be disposed of along with the vessel or reused when the mixing operation is complete.

52. The structure according to claim 51, wherein the sealable opening is provided in an upper portion of the vessel.

53. The structure according to claim 51, wherein the motive device includes a driving magnet structure, and the mixing element comprises a shaft carrying a disc-shaped permanent magnet at one end corresponding to the superconducting element, at least one pair of alternating polarity driven magnets at the opposite end corresponding to the driving magnet structure of the motive device, and at least one impeller.

54. A structure for intended use in pumping or mixing a fluid in a vessel in a non-contact fashion using a levitation device external to the vessel for providing a levitating force and a motive device external to the vessel for imparting rotary motion including a driving magnet structure, comprising:

a levitation magnet structure positioned adjacent to the levitation device;

a driven magnet structure positioned adjacent to the motive device, said driven magnet structure forming a magnetic coupling with the driving magnet structure;

a connector for connecting the levitation and driven magnet structures, whereby supplying the levitation and rotation of the structure externally avoids the need for shafts penetrating into or through the vessel or corresponding mechanical support bearings or seals.

55. The structure according to claim 54, wherein the driven magnet structure comprises at least one pair of alternating polarity magnets, whereby the magnets each form a portion of the magnetic coupling with the driving magnet structure on the motive device.

56. The structure according to claim 54, wherein the connector is a shaft that maintains the levitation and driving magnets in a vertically spaced relationship.

57. The structure according to claim 54, further including at least one impeller on the connector.

58. A method of levitating and rotating a magnetic structure in a vessel for the intended use of pumping or mixing at least a fluid, including a non-cryogenic fluid, comprising:

placing the magnetic structure in the vessel, said magnetic structure comprising a shaft carrying a levitation magnet at one end, at least one pair of alternating polarity driven magnets at the opposite end, and at least one impeller;

levitating the magnetic structure in the vessel using a superconducting element positioned in an evacuated or insulated chamber adjacent to the levitation magnet and thermally linked to a separate cooling source; and rotating the magnetic structure in the vessel by forming a magnetic coupling between a driving magnet structure on the motive device and the alternating polarity driven magnets of the magnetic structure.

59. A system for pumping or mixing a fluid in a vessel, comprising:

a magnetic element for placement in the vessel;

a superconducting element for levitating said magnetic element;

a structure defining a chamber around the superconducting element, said chamber being evacuated or insulated to thermally isolate the superconducting element from the vessel;

a closed-cycle refrigerator thermally linked to said superconducting element;

a motive device for rotating said magnetic element, whereby the fluid is pumped or mixed by the rotation of the magnetic element.

60. The system according to claim 59, wherein the motive device includes a driving magnet structure, and the magnetic element comprises a shaft carrying a disc-shaped permanent magnet at one end corresponding to the superconducting element, at least one pair of alternating polarity driven magnets at the opposite end corresponding to the driving magnet structure of the motive device, and at least one impeller for creating a pumping or mixing action in the fluid.

* * * * *

UNITED STATES PATENT AND TRADEMARK OFFICE
CERTIFICATE OF CORRECTION

PATENT NO. : 6,416,215 B1
DATED : July 9, 2002
INVENTOR(S) : Alexandre N. Terentiev It is certified that error appears in the above-identified patent and that said Letters Patent is hereby corrected as shown below:

Column 14,
Lines 52-53, change "superconduction" to -- superconducting --.

Signed and Sealed this

Twenty-seventh Day of August, 2002

*Attest:*

*Attesting Officer*

JAMES E. ROGAN
*Director of the United States Patent and Trademark Office*